United States Patent [19]

Tricoles et al.

[11] 4,255,702
[45] Mar. 10, 1981

[54] MEASUREMENT OF RADIANT ENERGY SCATTERING CHARACTERISTICS WITH A TURNTABLE-TYPE SCANNING APPARATUS

[75] Inventors: Gus P. Tricoles, San Diego; Eugene L. Rope, El Cajon, both of Calif.

[73] Assignee: General Dynamics/Electronics Division, San Diego, Calif.

[21] Appl. No.: 970,527

[22] Filed: Dec. 18, 1978

[51] Int. Cl.³ .............................................. G01R 27/04
[52] U.S. Cl. ............................. 324/58 B; 324/58.5 B
[58] Field of Search ................. 324/58 R, 58 A, 58 B, 324/58.5 R, 58.5 A, 58.5 B; 35/19 A, 19 B; 356/340

[56] References Cited
PUBLICATIONS

Welch Laboratory Apparatus (catalog); Sargent-Welch Sci. Co., Skokie, Ill.; 1968; p. 380.
Bickel et al.; Proc. Nat. Acad. Sci., U.S.; 73; 486; 1976.

*Primary Examiner*—Ernest F. Karlsen
*Attorney, Agent, or Firm*—Brown & Martin

[57] ABSTRACT

A method and apparatus for measuring radiant energy scattering characteristics of a test panel of dielectric material over a circular arc are disclosed. The test panel is supported on a turntable at a position on the axis of the turntable. The turntable has a fist antenna radially mounted thereon for rotation therewith and directed toward the position of the supported test panel. The test panel support is rotated with respect to the turntable to selectively position the test panel at a predetermined incidence angle with respect to the first antenna. The turntable is rotated with respect to a second antenna which is in a fixed stationary position and directed toward the supported position of the test panel to selectively position the test panel at an incidence angle with respect to the axis of propagation of the second antenna that is equal to and opposite the predetermined incidence angle. Radiation transmitted between the first and second antennas is measured with the test panel in the supported position at each of a plurality of predetermined equal and opposite incidence angles with respect to the first and second antennas; and radiation transmitted between the first and second antennas is measured at each of the plurality of predetermined incidence angles when the test panel is not supported on the turntable. The reflectance characteristics of the test panel are then determined by subtracting the measurements taken without the test panel in place from those taken with the test panel supported on the turntable.

13 Claims, 2 Drawing Figures

MEASUREMENT OF RADIANT ENERGY SCATTERING CHARACTERISTICS WITH A TURNTABLE-TYPE SCANNING APPARATUS

BACKGROUND OF THE INVENTION

The present invention is specifically directed to an improvement in methods and apparatus for measuring radiant energy scattering characteristics of a test panel. Radiant energy scattering characteristics include transmittance and reflectance characteristics.

In the prior art, the following apparatus is used to measure transmittance and reflectance characteristics of a planar sheet of dielectric material at microwave frequencies. A test panel of the dielectric material is positioned in an anechoic chamber with two microwave antennas.

To measure the transmittance characteristics of the test panel over a circular arc the two antennas are positioned so as to be directed toward each other along a common same axis of propagation, and the test panel is positioned between the two antennas along the common axis. The radiation between the antennas is measured with the test panel absent, and is also measured with the test panel present to determine the percentage of incident radiation that is transmitted through the test panel.

The plane of the test panel is supported along a second axis that is normal to the common axis of propagation of the antennas and is selectively rotated about the second axis to enable the transmittance characteristics of the panel to be measured at a plurality of predetermined incidence angles.

To measure the reflectance characteristics of the panel both antennas are positioned on the same side of the test panel and are directed at the test panel with their respective axes of propagation at predetermined equal and opposite incidence angles. For each of a plurality of different predetermined incidence angles at which measurements are taken both antennas are repositioned and redirected. This method and apparatus for measuring the reflectance characteristics is obviously quite cumbersome.

SUMMARY OF THE INVENTION

The present invention provides an improved scanning apparatus and method for measuring radiant energy scattering characteristics of a test panel.

The scanning apparatus includes a turntable; a support on the turntable for supporting a test panel in a selected position along the axis of the turntable; a first antenna radially mounted to the turntable for rotation with the turntable and directed toward the selected position of the supported test panel; and a second antenna in a fixed stationary position relative to the turntable and directed toward the selected position of a said supported test panel. Preferably, the support for the test panel is selectively rotatable with respect to the selected position on the turntable for enabling a supported test panel to be positioned at selected incidence angles with respect to the axis of propagation of the first antenna; and the test panel support is selectively translatable with respect to the turntable for enabling the plane of incidence of the supported test panel to be axially positioned on the turntable.

The method of the present invention for measuring radiant energy scattering characteristics of a test panel over a circular arc includes the steps of (a) supporting the test panel on a turntable at a position on the axis of the turntable, wherein the turntable has a first antenna radially mounted thereon for rotation therewith and directed toward the position of the supported test panel; (b) rotating the test panel with respect to the turntable to selectively position the test panel at a predetermined incidence angle with respect to the first antenna; (c) rotating the turntable with respect to a second antenna which is in a fixed stationary position and directed toward the supported position of the test panel to selectively position the test panel at an incidence angle with respect to the axis of propagation of the second antenna that is equal to and opposite the predetermined incidence angle; (d) measuring radiation transmitted between the first and second antennas with the test panel in the supported position at each of a plurality of predetermined equal and opposite incidence angles with respect to the first and second antennas; and (e) measuring radiation transmitted between the first and second antennas at each of the plurality of predetermined incidence angles when the test panel is not supported on the turntable.

The reflectance characteristics of the test panel are then determined by subtracting the measurements taken without the test panel in place from those taken with the test panel supported on the turntable.

The scanning apparatus of the present invention may be used for measuring both the reflectance and the transmittance characteristics of the test panel over a circular arc by continuously rotating the turntable so that the incidence angle of the test panel with respect to the axis of propagation of the second antenna continuously varies, and by continuously measuring the radiation transmitted between the first and second antennas as the turntable rotates to determine the angular distribution of energy reflected by and transmitted through the test panel. Such measurements are taken at each of the plurality of predetermined angles of incidence of the test panel with respect to the axis of propagation of the first antenna.

By scanning the measurements over a circular arc for each predetermined angle of incidence of the test panel with respect to the axis of propagation of the first antenna, the transmitted and reflected energy distributions are accurately determined and any endfire radiation caused by guided waves is thereby located.

The measurements that are made with the test panel removed also are taken continuously as the turntable rotates continuously.

Accordingly the same apparatus can be used conveniently for measuring both the reflectance and transmittance characteristics of a test panel.

Other features of the present invention are discussed in the description of the preferred embodiment.

DESCRIPTION OF THE PREFERRED EMBODIMENT

Figure 1:
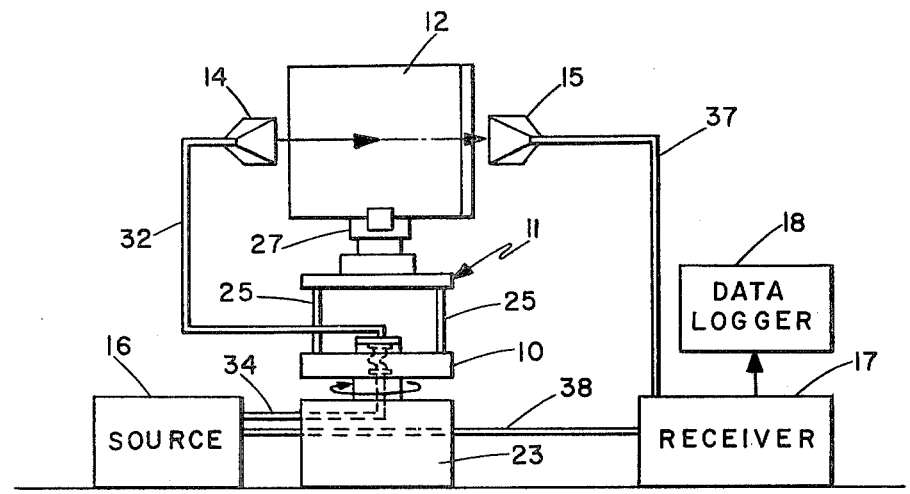
FIG. 1 is a partial perspective view and partial schematic block diagram showing the scanning apparatus of the present invention.
Figure 2:
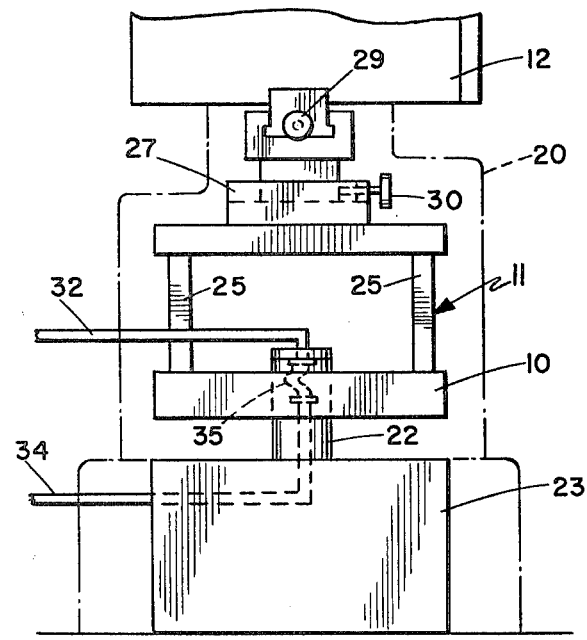
FIG. 2 is an enlarged view of a portion of the apparatus that is shown in perspective in FIG. 1.

Referring to FIGS. 1 and 2, a preferred embodiment of the scanning apparatus of the present invention includes a turntable 10, a support 11 for a test panel 12, a first antenna 14, a second antenna 15, a signal source 16, a receiver 17 and a data logger 18. The turntable 10, support 11, the first antenna 14 and the second antenna 15 are located within an anechoic chamber (not shown). The turntable 10 and support 11 are covered by absorbing material 20 (as shown in FIG. 2 by broken lines). The signal source 16, receiver 17 and the data logger 18 are located outside of the anechoic chamber. The turntable 10 is supported on a rotatable shaft 22, which is journaled in a bearing (not shown) within a turntable base 23. A motor (not shown) is positioned in the base 23 and coupled to the shaft 22 for continuously rotating the turntable 10.

The scanning apparatus is adapted for measuring the reflectance and transmittance characteristics of a test panel of a dielectric sheet material at microwave frequencies.

The support 11 is supported on the turntable 10 by columns 25. A lathe cross feed 27 is centered on the support 11 for axially supporting a test panel 12 on the turntable 10. The lathe cross feed has a channel for holding the test panel. The panel is translated by operation of manual control knobs 29 and 30, which control two micrometer drives and enable the test panel to be translated orthogonally in quarter-wavelength increments so as to enable the test panel 12 to be axially positioned on the turntable 10. The test panel 12 also may be rotated in the lathe cross feed to be disposed at a predetermined angle of incidence with respect to the axis of propagation of the first antenna 14.

The first antenna 14 is radially mounted on the turntable 10 by means of a waveguide section 32 for rotation with the turntable 10. The waveguide 32 is coupled to a waveguide 34, which extends from the signal source 16, by means of a waveguide rotating joint 35 which is positioned within the shaft 22 of the turntable 10. The waveguide rotating joint 35 enables the first antenna 14 to rotate with the turntable 10.

The first antenna 14 is directed so that its axis of propagation intersects the axis of the turntable 10.

The second antenna 15 is disposed in a fixed stationary position relative to the turntable 10 and is directed so that its axis of propagation also intersects the axis of the turntable 10. The second antenna 15 is connected to the receiver 17 by a waveguide 37. The waveguide 37 also serves to support the second antenna 15 in its fixed stationary position.

The receiver 17 also is connected to the signal source 16 by a waveguide loop 38. Microwave signals provided by the signal source are provided to the first antenna 14 via waveguides 34 and 32 and are transmitted by the first antenna 14. Microwave signals received by the second antenna 15 are provided to the receiver 17 via the waveguide 37. The receiver also receives reference signals from the signal source 16 via the waveguide loop 38, and is adopted for processing the signals received on waveguides 37 and 38 for measuring both the intensity and phase of the signals received by the second antenna 15 with respect to the signals transmitted by the first antenna 14. The waveguide loop 38 equalizes the lengths of the transmitted signal and the reference signal paths. A data logger 18 is connected to the receiver 17 for recording the measured intensity and phase data.

To make measurements of the reflectance and transmittance characteristics, first the test panel 12 is rotated in the lathe cross feed 27 to a predetermined incidence angle with respect to the axis of propagation of the first antenna 14. Then the turntable 10 is rotated continuously by the motor while microwave signals are transmitted by the first antenna 14 and received by the second antenna 15. Phase and intensity measurements are continuously recorded by the data logger 18 as the turntable 10 rotates. The procedure is repeated for each predetermined incidence angle which is changed by rotating the test panel 12 in the lathe cross feed 27 to a new selected position.

Transmittance characteristics measurements are recorded when the first and second antennas 14, 15 are on opposite sides of the test panel 12; and reflectance characteristics measurements are recorded when the first and second antennas 14, 15 are on the same side of the test panel 12.

Reflectance characteristics measurements also are taken and recorded with the test panel 12 covered by a metallic plate. The metallic plate data serves to normalize the phase and intensity based upon the assumption that the reflectance magnitude for the plate is "one". The lathe cross feed 27 is used to translate the metallic plate so that it is axially positioned on the turntable 10.

Data measurements are also recorded with the test panel absent as the turntable is rotated.

The transmittance and reflectance characteristics are determined from the measured data as follows:

For transmittance characteristics, let the measured radiation field with the panel present be $E_T$. Although the phase of $E_T$ is directly observable, the determination of $|E_T|$ requires assuming that intensity is proportional to $|E_T|^2$. The data are normalized to the incident (no panel) value $E_I$. Again intensity is assumed to be proportional to $|E_I|^2$. The transmittance (or complex transmission co-efficient is $T = E_T/E_I$.

The power transmittance is $|T|^2$, and the insertion phase delay is the argument (or phase) of T.

Determination of the reflectance characteristics requires subtracting the direct field $E_D$, i.e. the field measured with no panel present. Let $E_R$ represent the field with panel present and $E_M$ the field with the metal plate present. The fields $E_D$, $E_M$ and $E_R$ are complex-valued. The subtraction gives $E'_R$ the field reflected by the panel after subtracting the field coupled directly between the first and second antennas as $E'_R = E_R - E_D$.

For the field with the metal plate, the subtraction of the directly coupled field gives $E'_M = E_M - E_D$.

Reflectance (or complex reflection co-efficient) is $R = E'_R/E'_M$.

The power reflectance is $|R|^2$. The phase of the reflectance is the argument of R.

Approximate values of $|R|^2$ (but not the phase of R) also can be obtained without the metal plate data by normalizing the measured radiation field to the value measured when the axes of propagation of the first and second antennas are aligned. However, the method that uses the data with the metal plate gives more accurate results, and it is preferable because it gives the phase of R.

To determine the power absorptance $|A|^2$ assume that the quantities $|R|^2$ and $|T|^2$ are the only other wave mechanisms. Energy conservation provides that $$|A|^2 = 1 - |R|^2 - |T|^2$$

The above equation is approximate because $|R|^2$ and $|T|^2$ omit any energy radiated by the test panel as guided waves.

I claim:

1. A scanning apparatus, for enabling measurement of radiant energy scattering characteristics of a test panel, comprising a turntable;

support means on the turntable for supporting said test panel in a selected position along the axis of the turntable;

a first antenna radially mounted to the turntable for rotation with the turntable and directed toward the selected position of a said supported test panel; and a second antenna in a fixed stationary position relative to the turntable and directed toward the selected position of a said supported test panel.

2. A scanning apparatus according to claim 1, wherein the support means are selectively rotatable with respect to the selected position on the turntable for enabling a said supported test panel to be positioned at selected incidence angles with respect to the axis of propagation of the first antenna.

3. A scanning apparatus according to claim 2, wherein the support means are selectively translatable with respect to the turntable for enabling the plane of incidence of said supported test panel to be axially positioned on the turntable.

4. A scanning apparatus according to claim 3, comprising a lathe cross feed for rotating and translating the support means to selectively position said supported test panel.

5. A scanning apparatus according to claim 4, wherein the turntable has a hollow shaft that is rotatable with the turntable, and the support means are mounted above the turntable to provide access to the top of the hollow shaft, further comprising a first waveguide extending into the hollow shaft from the bottom of the shaft;

a waveguide rotating joint attached to the top of the hollow shaft and connected to the first waveguide; and a second waveguide connecting and mounting the first antenna to the waveguide rotating joint to connect the first antenna to the first waveguide and for enabling the first antenna to rotate with the turntable.

6. A scanning apparatus according to claim 1, wherein the turntable has a hollow shaft that is rotatable with the turntable, and the support means are mounted above the turntable to provide access to the top of the hollow shaft, further comprising a first waveguide extending into the hollow shaft from the bottom of the shaft;

a waveguide rotating joint attached to the top of the hollow shaft and connected to the first waveguide; and a second waveguide connecting and mounting the first antenna to the waveguide rotating joint to connect the first antenna to the first waveguide and for enabling the first antenna to rotate with the turntable.

7. A method of measuring radiant energy scattering characteristics of a test panel, comprising the steps of (a) supporting the test panel on a turntable at a position on the axis of the turntable, wherein the turntable has a first antenna radially mounted thereon for rotation therewith and directed toward the position of the supported test panel;

(b) rotating the test panel with respect to the turntable to selectively position the test panel at a predetermined incidence angle with respect to the axis of propagation of the first antenna;

(c) rotating the turntable with respect to a second antenna which is in a fixed stationary position and directed toward the supported position of the test panel to selectively position the test panel at an incidence angle with respect to the axis of propagation of the second antenna that is equal to and opposite the predetermined incidence angle;

(d) measuring radiation transmitted between the first and second antennas with the test panel in said supported position at each of a plurality of predetermined equal and opposite incidence angles with respect to the first and second antennas; and (e) measuring radiation transmitted between the first and second antennas at each of said plurality of predetermined incidence angles when the test panel is not supported on the turntable.

8. A method according to claim 7, wherein step (c) comprises continuously rotating the turntable so that the incidence angle of the test panel with respect to the axis of propagation of the second antenna continuously varies; and step (d) further comprises continuously measuring radiation transmitted between the first and second antennas as the turntable rotates to determine the angular distribution of energy reflected by and transmitted through the test panel.

9. A method according to claim 8, wherein step (e) comprises continuously rotating the turntable and continuously measuring radiation transmitted between the first and second antennas as the turntable rotates to determine the angular distribution of energy transmitted between the first and second antennas over a circular arc without the test panel supported on the turntable.

10. A method according to claim 7, wherein step (e) comprises continuously rotating the turntable and continuously measuring radiation transmitted between the first and second antennas as the turntable rotates to determine the angular distribution of energy transmitted between the first and second antennas over a circular arc without the test panel supported on the turntable.

11. A method according to claims 7 or 8 further comprising the step of:

(f) measuring radiation transmitted between the first and second antennas at each of said plurality of predetermined incidence angles when the test panel supported on the turntable has known reflectance characteristics.

12. A method according to claim 11, wherein the test panel in step (f) is a metallic plate.

13. A scanning interferometer according to claims 1 or 6, further comprising:

a motor coupled to the turntable for continuously rotating the turntable.

* * * * *